(12) United States Patent
Bo et al.

(10) Patent No.: US 12,053,714 B2
(45) Date of Patent: Aug. 6, 2024

(54) PHOTOTHERMAL EVAPORATION MATERIAL INTEGRATING LIGHT ABSORPTION AND THERMAL INSULATION, PREPARATION APPLICATION THEREOF, USE THEREOF

(71) Applicant: ZHEJIANG UNIVERSITY, Hangzhou (CN)

(72) Inventors: Zheng Bo, Hangzhou (CN); Shenghao Wu, Hangzhou (CN); Huachao Yang, Hangzhou (CN); Jianhua Yan, Hangzhou (CN); Kefa Cen, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 1068 days.

(21) Appl. No.: 16/960,067

(22) PCT Filed: Dec. 20, 2019

(86) PCT No.: PCT/CN2019/126848
§ 371 (c)(1),
(2) Date: Jul. 3, 2020

(87) PCT Pub. No.: WO2020/224267
PCT Pub. Date: Nov. 12, 2020

(65) Prior Publication Data
US 2021/0253431 A1   Aug. 19, 2021

(30) Foreign Application Priority Data

| May 6, 2019 | (CN) | ......................... | 201910370638.7 |
| May 6, 2019 | (CN) | ......................... | 201910370640.4 |
| May 6, 2019 | (CN) | ......................... | 201910370668.8 |

(51) Int. Cl.
*B01D 1/00* (2006.01)
*A61L 2/07* (2006.01)
(Continued)

(52) U.S. Cl.
CPC ............. *B01D 1/0035* (2013.01); *A61L 2/07* (2013.01); *A61L 2/26* (2013.01); *B01D 5/006* (2013.01);
(Continued)

(58) Field of Classification Search
None
See application file for complete search history.

(56) References Cited

U.S. PATENT DOCUMENTS

2010/0035093 A1* 2/2010 Ruoff ..................... H01G 11/36
                                                              29/25.03
2012/0322917 A1* 12/2012 Alcazar Jorba ....... C01B 32/194
                                                              516/15
(Continued)

FOREIGN PATENT DOCUMENTS

CN        104927791           9/2015
CN        106517158 A    *    3/2017
(Continued)

OTHER PUBLICATIONS

Liu, Z. et al., Preparation Method of Photothermal Conversion, Nov. 3, 2017, machine translation of CN 107311467 (Year: 2017).*
(Continued)

*Primary Examiner* — Chinessa T. Golden
(74) *Attorney, Agent, or Firm* — Jiwen Chen; Joywin IP Law PLLC

(57) ABSTRACT

The invention discloses a photothermal evaporation material integrating light absorption and thermal insulation, comprising a heat insulator and a light absorber that covers the external surface of the heat insulator, the light absorber is
(Continued)

vertically-oriented graphene, the heat insulator is a graphene foam, and the vertically-oriented graphene and graphene foam are connected by covalent bonds; the light absorber is vertically-oriented graphene whose surface is modified with hydrophilic functional groups. The invention also discloses a method for fabricating the photothermal evaporation material integrating light absorption and thermal insulation. The invention also discloses a solar energy photothermal seawater desalination device and a high-temperature steam sterilization device. The photothermal evaporation material integrating light absorption and thermal insulation overcomes the problem of easy separation between the light absorber and the heat insulator, realizes rapid and efficient photothermal evaporation, and improves the stability and photothermal conversion efficiency of the solar photothermal seawater desalination device and the high-temperature steam sterilization device.

9 Claims, 9 Drawing Sheets

(51) Int. Cl.
| | | |
|---|---|---|
| A61L 2/26 | (2006.01) | |
| B01D 5/00 | (2006.01) | |
| C01B 32/186 | (2017.01) | |
| C01B 32/194 | (2017.01) | |
| C01B 32/198 | (2017.01) | |
| C02F 1/14 | (2023.01) | |
| C23C 16/26 | (2006.01) | |
| C23C 16/50 | (2006.01) | |
| C23C 16/56 | (2006.01) | |
| C02F 103/08 | (2006.01) | |

(52) U.S. Cl.
CPC .......... *C01B 32/186* (2017.08); *C01B 32/194* (2017.08); *C01B 32/198* (2017.08); *C02F 1/14* (2013.01); *C23C 16/26* (2013.01); *C23C 16/50* (2013.01); *C23C 16/56* (2013.01); *A61L 2202/11* (2013.01); *A61L 2202/122* (2013.01); *C01B 2204/24* (2013.01); *C01P 2006/60* (2013.01); *C02F 2103/08* (2013.01)

(56) References Cited

U.S. PATENT DOCUMENTS

| | | | |
|---|---|---|---|
| 2015/0374868 A1* | 12/2015 | Bruce | A61L 2/26 422/119 |
| 2017/0066932 A1* | 3/2017 | Magdassi | C03C 17/32 |
| 2017/0121177 A1 | 5/2017 | Silva et al. | |
| 2018/0356127 A1* | 12/2018 | Hu | B01D 1/0005 |

FOREIGN PATENT DOCUMENTS

| | | |
|---|---|---|
| CN | 106865528 | 6/2017 |
| CN | 106892476 | 6/2017 |
| CN | 107311467 | 11/2017 |
| CN | 107311467 A * | 11/2017 |

OTHER PUBLICATIONS

Liu, Z., Preparation Method of Photothermal Conversion, Nov. 3, 2017, machine translation of CN 107311467 (Year: 2017).*
Wang, Method of Preparing Graphene Foam Material, Mar. 22, 2017, machine translation of CN 106517158 (Year: 2017).*
VH Dalvi et al., Nat, Clim. Change 2015, 5: 1007-1013.
H. Ghasemi et al. Nat. Commun. 2014, 5: 4449.
L. Zhou et al. Sci. Adv. 2016, 2: e1501227.
Q. Jiang et al. Adv. Mater. 2016, 28: 9400-9407.

* cited by examiner

PHOTOTHERMAL EVAPORATION MATERIAL INTEGRATING LIGHT ABSORPTION AND THERMAL INSULATION, PREPARATION APPLICATION THEREOF, USE THEREOF

This is a U.S. national stage application of PCT Application No. PCT/CN2019/126848 under 35 U.S.C. 371, filed Dec. 20, 2019 in Chinese, claiming priority of Chinese Application No. 201910370638.7, filed May 6, 2019; Application No. 201910370640.4, filed May 6, 2019; and Application No. 201910370668.8, filed May 6, 2019, all of which are hereby incorporated by reference.

TECHNICAL FIELD

The present invention belongs to the field of solar photothermal utilization, and particularly relates to a photothermal evaporation material integrating light absorption and thermal insulation, preparation application thereof, use thereof.

DESCRIPTION OF RELATED ART

Solar energy is the most widely-distributed energy with the largest reserves on the planet. Because of its clean and renewable characteristics, it has received the most widespread attention in the 21st century when the energy crisis and environmental problems are becoming more and more serious. Photothermal conversion is one of the most important forms of solar energy utilization. How to convert solar energy to thermal energy efficiently and cost-effectively, and how to use the converted thermal energy effectively are becoming a current international research hotspot [V H Dalvi et al. *Nat, Clim. Change* 2015, 5: 1007-1013].

In 2014, the Gang Chen group of the Massachusetts Institute of Technology proposed a localized heating system with a double-layer structure (consisting of light absorber and heat insulator), which can efficiently use solar energy to generate steam. It reduces the energy loss caused by heat dissipation from the liquid to the environment, and improves the solar-thermal conversion efficiency [H. Ghasemi et al. *Nat. Commun.* 2014, 5: 4449]. Subsequent works have further optimized the double-layer structure of the localized heating system, such as developing light absorbers with high light absorption and heat insulators with excellent thermal insulation performance [L. Zhou et al. *Sci. Adv.* 2016, 2: e1501227; Q. Jiang et al. *Adv. Mater* 2016, 28: 9400-9407].

However, in the previously reported localized heating systems, there are two problems: (1) The localized heating system is a double-layer structure composed of light absorbers stacked directly on the upper surface of the heat insulator. During the practical evaporation process, the upper light absorber is easily detached from the underneath heat insulator, the gap between the upper light absorber and the lower heat insulator is filled by the liquid that will be evaporated; thus the thermal insulation performance of the localized heating system is deteriorated. In addition, the separation of the light absorber and the heat insulator will reduce the mechanical stability of the system, which is not conducive to the long-term operation of the localized heating system. (2) The liquid transports through the interior of the lower heat insulator before exchanging heat with the upper light absorber and then evaporating; and thus the liquid with high thermal conductivity (such as water, whose thermal conductivity is 0.6 $Wm^{-1}K^{-1}$) permeates into the heat insulator, and will also cause the deterioration of the thermal insulation performance, which in turn will increase the heat dissipation loss and decrease the photothermal conversion in practical operation.

SUMMARY OF THE DISCLOSURE

The object of the present invention is to provide a photothermal evaporation material integrating light absorption and thermal insulation. The photothermal evaporation material integrating light absorption and thermal insulation provided by the present invention overcomes the problems of easy separation of the light absorber and the heat insulator, and the problem of heat loss caused by the liquid penetrating into the heat insulator, and improves the stability and photothermal conversion of the localized heating system. It can realize fast and efficient photothermal evaporation. The preparation process of the photothermal evaporation material integrating light absorption and thermal insulation is simple and easy to be mass-produced. It can be used in seawater desalination, sewage purification, and high-temperature steam sterilization.

A photothermal evaporation material integrating light absorption and thermal insulation, the photothermal evaporation material integrating light absorption and thermal insulation comprises a heat insulator and a light absorber that covers the external surface of the heat insulator, the light absorber is vertically-oriented graphene, the heat insulator is a graphene foam, and the vertically-oriented graphene and graphene foam are connected by covalent bonds; the light absorber is vertically-oriented graphene whose surface is modified with hydrophilic functional groups.

The light absorber captures solar energy and converts solar energy into thermal energy to generate a local high temperature; the heat insulator blocks heat transport and reduces heat dissipation.

The vertically-oriented graphene consists of a carbon nanowall array. The graphene foam has a porous structure.

The vertically-oriented graphene modified with hydrophilic functional groups can be used as a liquid flow channel to transport liquid to a local high-temperature area through capillary action, so as to achieve rapid photothermal evaporation; and to protect the insulator from being wetted by the liquid.

The hydrophilic functional groups are oxygen-containing functional groups. The oxygen-containing functional groups are selected from one or a combination of at least two of hydroxyl (—OH), aldehyde group (—CHO), and carboxyl (—COOH). —OH, —CHO and —COOH are hydrophilic groups, and one or at least two of the above hydrophilic functional groups are modified on the surface of the vertically-oriented graphene, which can enhance the affinity between the vertically-oriented graphene and water, and enhance the capillary action of the vertically-oriented graphene.

The absorbance of the light absorber is 90-99%, and the thermal conductivity of the heat insulator is 0.02-0.2 W $m^{-1}$ $K^{-1}$.

Preferably, the absorbance of the light absorber is 97.0-98.2%, and the thermal conductivity of the heat insulator is 0.031-0.041 W $m^{-1}$ $K^{-1}$.

The present invention also provides an application of the photothermal evaporation material integrating light absorption and thermal insulation, the photothermal evaporation material integrating light absorption and thermal insulation is used for seawater desalination, sewage purification, and high-temperature steam sterilize.

The present invention also provides a solar photothermal seawater desalination device, which has a simple structure, is easy to operate, can efficiently collect condensate water, and solves the light-blocking problem of condensate water and steam. The stability and photothermal conversion efficiency of the solar photothermal seawater desalination device both increase significantly, and the salinity decrease significantly after the desalination process.

A solar photothermal seawater desalination device, the solar photothermal seawater desalination device comprises a light-transmissive condensation plate, photothermal evaporation material, an evaporation chamber, and a collection chamber in order from top to bottom. The light-transmissive condensation plate covers the evaporation chamber and guides the condensate water to the collection chamber. The photothermal evaporation material is placed in the evaporation chamber. The photothermal evaporation material comprises a heat insulator and a light absorber that covers the external surface of the heat insulator. The light absorber is vertically-oriented graphene. The heat insulator is graphene foam, and the vertically-oriented graphene and graphene foam are connected by covalent bonds. The light absorber is vertically-oriented graphene whose surface is modified with hydrophilic functional groups.

The oxygen-containing functional groups are selected from one or a combination of at least two of hydroxyl (—OH), aldehyde group (—CHO), and carboxyl (—COOH). —OH, —CHO and —COOH are hydrophilic groups, and one or at least two of the above hydrophilic functional groups are modified on the surface of the vertically-oriented graphene, which can enhance the affinity between the vertically-oriented graphene and water, and enhance the capillary action of the vertically-oriented graphene.

The absorbance of the light absorber is 90-99%, and the thermal conductivity of the heat insulator is 0.02-0.2 $W\ m^{-1}\ K^{-1}$. Preferably, the absorbance of the light absorber is 97.0-98.2%, and the thermal conductivity of the heat insulator is 0.031-0.041 $W\ m^{-1}\ K^{-1}$.

The collection chamber is provided with a collection port, the light-transmissive condensation plate is covered on the evaporation chamber and extends to the collection port on the collection chamber to guide the condensate water to the collection chamber.

Preferably, the evaporation chamber and the collection chamber are an integrated structure.

The solar photothermal seawater desalination device further comprises an extraction channel and a steam guiding conduit, one end of the extraction channel is connected to the evaporation chamber, the other end is connected to the collection chamber through the steam guiding conduit; the suction channel and the steam guiding conduit are provided on the side wall of the evaporation chamber.

Preferably, the solar photothermal seawater desalination device further comprises an extraction fan and a driving device provided in the extraction channel, and the driving device drives the extraction fan to pump the steam in the evaporation chamber to the steam guiding conduit.

Preferably, the driving device is a solar panel.

The evaporation chamber is used to store seawater and photothermal evaporation materials. The photothermal evaporation material floats on the seawater and evaporates the seawater by photothermal conversion to generate steam. The light-transmissive condensation plate covers the evaporation chamber to prevent steam from spilling out, the steam condenses on the light-transmissive condensation plate and flows to the collection chamber along the light-transmissive condensation plate. The side wall of the evaporation chamber is provided with an extraction channel, and the extraction fan is installed in the extraction channel to pump the steam in the evaporation chamber. The steam guiding conduit is connected with the extraction channel and the collection chamber, and the steam absorbed by the extraction fan is transmitted to the collection chamber by the steam guiding conduit, and is condenses in the collection chamber. The solar panel is used for photovoltaic power generation and provides electric energy for the extraction fan.

The solar photothermal seawater desalination device further comprises a water inlet of the evaporation chamber and a water outlet of the evaporation chamber, the water inlet of the evaporation chamber supplements seawater to the evaporation chamber, and the water outlet of the evaporation chamber discharges the seawater in the evaporation chamber; the solar photothermal seawater desalination device also comprises a water inlet of the collection chamber and a water outlet of the collection chamber.

The light-transmissive condensation plate is transparent.

The output voltage of the solar panel is within the working voltage range of the extraction fan. The output voltage of the solar panel and the working voltage of the extraction fan are related to the size of the device. The larger the volume of the device is, the higher the output voltage and the output power of the solar panel are required.

During the operation of the solar photothermal seawater desalination device, the internal space is sealed, the water inlet of the evaporation chamber and the water outlet of the evaporation chamber are closed, and the water inlet of the collection chamber and the water outlet of the collection chamber are closed. In the process of cleaning the evaporation chamber, the water inlet of the evaporation chamber and the water outlet of the evaporation chamber are opened.

The inclination angle of the light-transmissive condensation plate is 10°-60°. The inclination is horizontal and downward.

Preferably, the inclination angle of the light-transmissive condensation plate is 30°.

The evaporation chamber and the collection chamber are distributed up and down, wherein the evaporation chamber is located above the collection chamber.

The position of the extraction channel is higher than that of the photothermal evaporation material. It is used to prevent seawater from flowing into the collection chamber through the extraction channel.

The present invention also provides a high-temperature steam sterilization device, which utilizes the widely-distributed, green and clean solar energy as the driving force, does not consume electrical energy, and has a wide range of applications. The device has simple structure, small volume, portable and simple operation. The invention uses the photothermal evaporation material that can capture solar energy and meanwhile block heat loss, greatly increasing the photothermal conversion efficiency of the device and leading to the short sterilization time and the excellent sterilization performance.

A high-temperature steam sterilization device, the high-temperature steam sterilization device comprises a steam chamber, an optical concentrator covering the steam chamber, a loading tray, and a water storage cup assembled inside the steam chamber, and a photothermal evaporation material in the water storage cup. The photothermal evaporation material comprises a heat insulator and a light absorber that covers the external surface of the heat insulator, the light absorber is vertically-oriented graphene, the heat insulator is graphene foam, and the vertically-oriented graphene and graphene foam are connected by covalent bonds; the light absorber is vertically-oriented graphene whose surface is modified with hydrophilic functional groups.

The hydrophilic functional groups are oxygen-containing functional groups. The oxygen-containing functional groups are selected from one or a combination of at least two of hydroxyl (—OH), aldehyde group (—CHO), and carboxyl (—COOH). —OH, —CHO and —COOH are hydrophilic groups, and one or at least two of the above hydrophilic functional groups are modified on the surface of the vertically-oriented graphene, which can enhance the affinity between the vertically-oriented graphene and water, and enhance the capillary action of the vertically-oriented graphene.

The absorbance of the light absorber is 90-99%, and the thermal conductivity of the heat insulator is 0.02-0.2 W m$^{-1}$ K$^{-1}$. Preferably, the absorbance of the light absorber is 97.0-98.2%, and the thermal conductivity of the heat insulator is 0.031-0.041 W m$^{-1}$ K$^{-1}$.

Preferably, the loading tray has a plurality of through holes in the vertical direction. After the steam condenses, it flows to the bottom of the steam chamber through the through-holes to avoid the condensed water adhering to the object to be sterilized and affect the sterilization effect.

The optical concentrator focuses the light beam into the water storage cup.

Preferably, the cross-sectional shape of the optical concentrator and the water storage cup are the same, and the cross-sectional area ratio is 10-100:1, and the optical concentrator and the water storage cup are assembled concentrically.

Preferably, the steam chamber is provided with a pallet for mounting the loading tray.

Preferably, a groove is provided in the center of the loading tray, and the size of the groove is equivalent to the size of the bottom of the water storage cup. The groove is used to fix the installation position of the water storage cup to ensure the concentric assembly relationship between the water storage cup and the optical concentrator.

Preferably, the high-temperature steam sterilization device further comprises a sealing ring and a clamp for fixing the optical concentrator.

The loading tray is placed on the pallet of the evaporation chamber; the water storage cup is placed in the groove in the center of the loading tray; a certain amount of water is added to the water storage cup, and the photothermal evaporation material is put into the water storage cup from above, the photothermal evaporation material floats on the surface of the water; the items to be sterilized is placed on the loading tray in the evaporation chamber; then the optical concentrator is covered on the evaporation chamber to concentrate the incident light to the upper surface of the photothermal evaporation material and prevent the steam from overflowing; and the evaporation chamber is sealed with a sealing ring, a fixing ring, and a clamp.

A method for fabricating the photothermal evaporation material integrating light absorption and thermal insulation, comprising the following steps:

(1) Preparing an aqueous solution of graphene oxide;
(2) Transferring the aqueous solution of graphene oxide obtained in step (1) to a high temperature and high-pressure reactor for hydrothermal reaction, and cooling to obtain a graphene hydrogel;
(3) Soaking the graphene hydrogel obtained in step (2) with an ethanol aqueous solution;
(4) Transferring the graphene hydrogel to a freezing chamber for freezing, and then transferring to a drying chamber for vacuum drying to obtain a graphene foam;
(5) Placing the obtained graphene foam in a plasma-enhanced chemical vapor deposition reaction chamber, and introducing methane or a mixture of hydrogen and methane. After the chemical vapor deposition reaction, an inert gas is introduced for cooling to obtain vertically-oriented graphite/graphene foam;
(6) Exposing the vertically-oriented graphene/graphene foam obtained in step (5) to an ozone environment, and hydrophilic functional groups are modified on the surface of the vertically-oriented graphene to obtain a photothermal evaporation material integrating light absorption and thermal insulation.

Preferably, the aqueous solution of graphene oxide in step (1) further comprises an additive, and the additive comprises sodium tetraborate decahydrate, amine compound or mixtures thereof; the concentration of the graphene oxide is 1-10 g L$^{-1}$, the concentration of the sodium tetraborate decahydrate is 0-10 mmol L$^{-1}$, the concentration of the amine compound is 0-100 mmol L$^{-1}$; and the concentration of the sodium tetraborate decahydrate and the concentration of the amine compound are not 0 at the same time.

The concentration of graphene oxide is directly related to the density, mechanical strength, thermal conductivity, and preparation cost of the obtained graphene foam. When the concentration of graphene oxide increases, the density of graphene foam increases, the mechanical strength increases, the thermal conductivity increases, and the manufacturing cost increases; when the graphene oxide concentration is less than 1 g L$^{-1}$, the mechanical strength of the obtained graphene foam is weak and easy to be damaged in the process of practical application; when the concentration of graphene oxide is greater than 10 g L$^{-1}$, the density and thermal conductivity of the obtained graphene foam increase, which will weaken the photothermal conversion efficiency in the application of photothermal evaporation, and the increase of preparation costs is not conducive to the practical application of the material.

Sodium tetraborate is used as a structural strengthening agent in the synthesis process of graphene hydrogel, which can enhance the mechanical strength of graphene foam. In addition, sodium tetraborate promotes agglomeration during the hydrothermal reaction, which in turn affects the thermal conductivity of graphene foam. The concentration of the amine compound also affects the thermal conductivity and mechanical strength of the graphene foam.

Preferably, the aqueous solution of graphene oxide in step (1) comprises graphene oxide, sodium tetraborate decahydrate, and amine compound at concentrations of 4-6 g L$^{-1}$, 1-5 mmol L$^{-1}$, and 4-20 mmol L$^{-1}$.

When the concentration of graphene oxide is 4-6 g L$^{-1}$, the obtained graphene foam has good mechanical properties, meanwhile low density, and thermal conductivity.

When the concentration of sodium tetraborate decahydrate is less than 1 mmol L$^{-1}$, the structure strengthening effect of sodium tetraborate is weak, and the obtained graphene foam structure is unstable and easy to be damaged. When the concentration of sodium tetraborate decahydrate is more than 5 mmol L$^{-1}$, the agglomeration phenomenon is more serious, resulting in a higher thermal conductivity of the obtained graphene foam.

When the concentration of the amine compound is less than 4 mmol L$^{-1}$, the effect of the amine compound on blocking agglomeration is weak, and the thermal conductivity of the obtained graphene foam is relatively high. When the concentration of the amine compound is more than 20 mmol L$^{-1}$, the structure of the obtained graphene foam is fluffy and the mechanical strength is weak.

The amine compound is selected from one or a combination of at least two of ethylenediamine, butanediamine, hexanediamine, and cyclohexanediamine. The diamine amine-based compounds have two amino groups, which are easy to polycondensate with graphene oxide. They exist stably between graphene sheets and act as links and supports, and hinder the agglomeration of graphene to obtain porous structures.

Preferably, the amine compound is ethylenediamine. The molecular sizes of the four amine compounds of ethylenediamine, butanediamine, hexamethylenediamine, and cyclohexanediamine are in the following order: ethylenediamine<butanediamine<hexanediamine<cyclohexanediamine. A larger molecular spacer will lead to a weaker mechanical strength, require more structural strengthening agents, and require a higher synthesis temperature and a longer synthesis time. So, ethylenediamine, as the smallest molecular size of diamine compounds, is the preferred agent when it has sufficed the application requirements.

The conditions of hydrothermal reaction in step (2) are: the reaction temperature is 90-180° C.; the reaction time is 6-18 hours.

The reaction temperature and reaction time will affect the degree of graphitization and agglomeration of graphene hydrogel. Increasing the temperature and prolonging time can improve the graphitization degree of graphene hydrogel, promote the agglomeration of graphene oxide and the formation of graphene hydrogel, and enhance the mechanical strength of the obtained graphene foam.

When the reaction temperature is less than 90° C. or the reaction time is less than 6 hours, the hydrothermal reaction process will be inadequate, the graphene hydrogel cannot be formed or the mechanical strength of the final graphene foam is weak. When the reaction temperature is greater than 180° C. or the reaction time is greater than 18 hours, it will cause serious agglomeration, leading to relatively high density and thermal conductivity of the obtained graphene foam.

In step (3), the cleaning method is to soak the graphene hydrogel with an ethanol aqueous solution for 6-24 hours, wherein the ethanol volume fraction of the ethanol aqueous solution is 10%-30%.

In step (4), the temperature of the freezing chamber is −80 to −10° C., and the freezing time is 6-24 hours; the temperature of the drying chamber is −20 to 0° C., the air pressure of the drying chamber is <650 Pa and the drying time is 6-48 hours.

In step (5), the flow ratio of the gas mixture of hydrogen and methane is 0-20:1.

The flow ratio of $H_2$ and $CH_4$ is the key to synthesize vertically-oriented graphene. When the flow ratio of $H_2$ and $CH_4$ is greater than 20:1, the obtained composition is not vertically-oriented graphene; and the flow ratio of $H_2$ and $CH_4$ will affect the morphology and chemical properties of the compound.

Preferably, in step (5), the flow ratio of $H_2$ and $CH_4$ is 1-5:1. When the flow ratio is less than 1:1, the synthesis speed is slow. When the flow ratio is more than 5:1, the morphology and chemical properties of the obtained compound are closer to amorphous carbon, carbon nanofibers, and carbon nanotubes.

In step (5), the reaction conditions of the chemical vapor deposition reaction are: the synthesis temperature is 500-1000° C., the synthetic gas pressure is 10-1000 Pa. When the temperature is less than 500° C., vertically-oriented graphene cannot be synthesized. When the temperature is more than 1000° C., it is beneficial to accelerate the synthesis speed of vertically-oriented graphene; however, the technological requirements for the equipment and the energy consumption are relatively high, which is not conducive to practical applications. When the air pressure is less than 10 Pa, the technological requirements of the equipment are high, which is difficult to achieve. When the air pressure is more than 1000 Pa, higher temperature and higher power are required, which is not conducive to practical applications.

Preferably, in step (5), the reaction conditions of the chemical vapor deposition reaction are: the synthesis temperature is 600-800° C., and the synthesis gas pressure is 10-500 Pa. The speed of synthesis of vertically-oriented graphene is moderate and the energy consumption is small, and the performance meets the requirements, which is conducive to practical applications.

In step (5), the plasma source in the chemical vapor deposition reaction is selected from microwave plasma, inductively coupled plasma, or direct current glow discharge plasma, with a power of 200-500 W and a synthesis time of 1-180 min.

When the synthesis time is less than 1 min, the amount of vertically-oriented graphene synthesized is less, and the light absorptance is lower. When the synthesis time is greater than 180 min, there is no significant improvement in the light absorptance and photothermal evaporation performance, resulting in raw materials and energy waste.

Preferably, maintaining for 10-120 min, an appropriate amount of vertically-oriented graphene is synthesized.

In step (5), an inert gas is used as the cooling gas, with a flow ratio of 10-100 ml min$^{-1}$.

In step (6), the method for generating modified hydrophilic functional groups on the surface of the vertically-oriented graphene is to expose the vertically-oriented graphene/graphene foam obtained in the step (5) to an environment with an ozone concentration of 200 ppm for 1-10 min, the hydrophilic functional groups are modified on the surface of vertically-oriented graphene. Specifically, ozone is generated by a dielectric barrier discharge device, and the air is used as the feeding gas.

Preferably, the vertically-oriented graphene/graphene foam is exposed to an environment with an ozone concentration of 200 ppm for 2-4 minutes. In this range, the vertically-oriented graphene whose surface is modified with oxygen-containing functional groups can obtain good hydrophilicity, while the internal graphene foam can maintain its super-hydrophobicity.

Compared with the prior art, the present invention has the following beneficial effects:

The photothermal evaporation material integrating light absorption and thermal insulation provided by the present invention connects the light absorber and the heat insulator with covalent bonds, which has the functions of capturing solar energy and blocking heat flow loss, overcomes the problem of easy separation between the light absorber and the heat insulator in the localized heating system, and improves the stability of the system.

The light absorber of the photothermal evaporation material integrating light absorption and thermal insulation provided by the present invention can also be used as a liquid flow channel to protect the heat insulator from being wetted by the liquid, and prevent the heat flow loss caused by the infiltrated liquid. The heat loss caused by the penetration of liquid into the heat insulator of the localized heating system is thus solved, and the efficiency of photothermal conversion of the system is improved. The photothermal evaporation material integrating light absorption and thermal insulation provided by the present invention realizes fast and efficient photothermal evaporation, the scalable preparation is easy to be achieved. It can be used in seawater desalination, sewage purification, and high-temperature steam sterilization.

The solar photothermal seawater desalination device provided by the present invention has the characteristics of simple structure and easy operation. The solar photothermal seawater desalination device provided by the present invention can collect condensate water efficiently, solve the light-blocking problem of condensate water and steam, and improve the stability of the photothermal seawater desalination system and the photothermal conversion efficiency.

The high-temperature steam sterilization device provided by the present invention utilizes the widely-distributed, green and clean solar energy as the driving force, does not consume electric energy, and has a wide range of applications. The high-temperature steam sterilization device provided by the present invention is based on integrated design, has no complicated structure, has low processing cost, and is easy to mass process and produce. The high-temperature steam sterilization device provided by the invention has a small volume, and is convenient to carry and easy to operate. The present invention greatly improves the stability of the device and the photothermal conversion by using the photothermal evaporation materials that can capture solar energy and meanwhile block heat flow loss, and generate steam quickly, leading to short sterilization time and excellent sterilization performance.

DESCRIPTION OF THE EMBODIMENTS

In order to make the present invention more understandable, the technical solution of the present invention will be further described below with reference to the drawings and specific embodiments. The embodiments described below are only for explaining the present invention, and are not intended to limit the present invention in any form or in substance.

Figure 1:
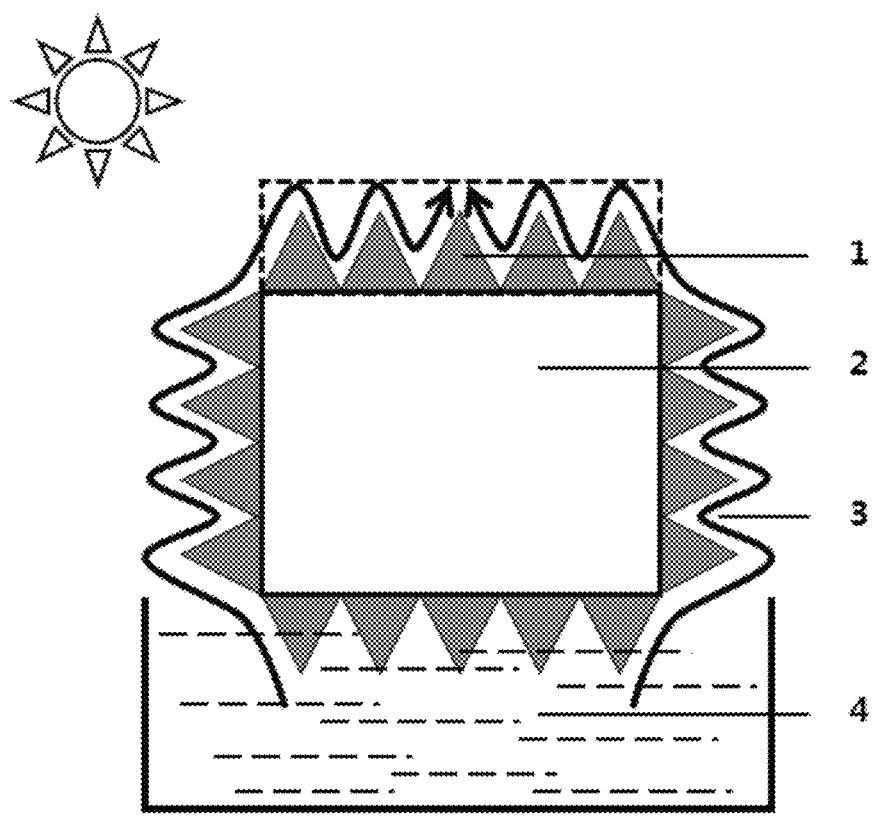
FIG. 1 is a schematic structural view of a photothermal evaporation material integrating light absorption and thermal insulation provided by the present invention.

As shown in FIG. 1, the photothermal evaporation material integrating light absorption and thermal insulation provided by the present invention comprises a heat insulator 2 and a light absorber 1 covering the external surface of the heat insulator 2. The light absorber 1 was vertically-oriented graphene whose surface is modified with hydrophilic functional groups. The heat insulator 2 was graphene foam, and the vertically-oriented graphene and graphene foam were connected by covalent bonds. The light absorber was vertically-oriented graphene whose surface was modified with hydrophilic functional groups.

The light absorber 1 captured solar energy and converted solar energy into thermal energy to generate a local high temperature. The heat insulator 2 blocked heat transport and reduced heat dissipation. At the same time, the light absorber 1 also served as a liquid flow channel 3, sucking the liquid 4 through capillary action, so that the liquid 4 reached the local high-temperature area, and realized rapid light and heat evaporation. At the same time, the liquid flow channel 3 can protect the heat insulator 2 from being wetted by the liquid 4 and prevent the heat flow loss caused by the infiltrated liquid 4.

Figure 2:
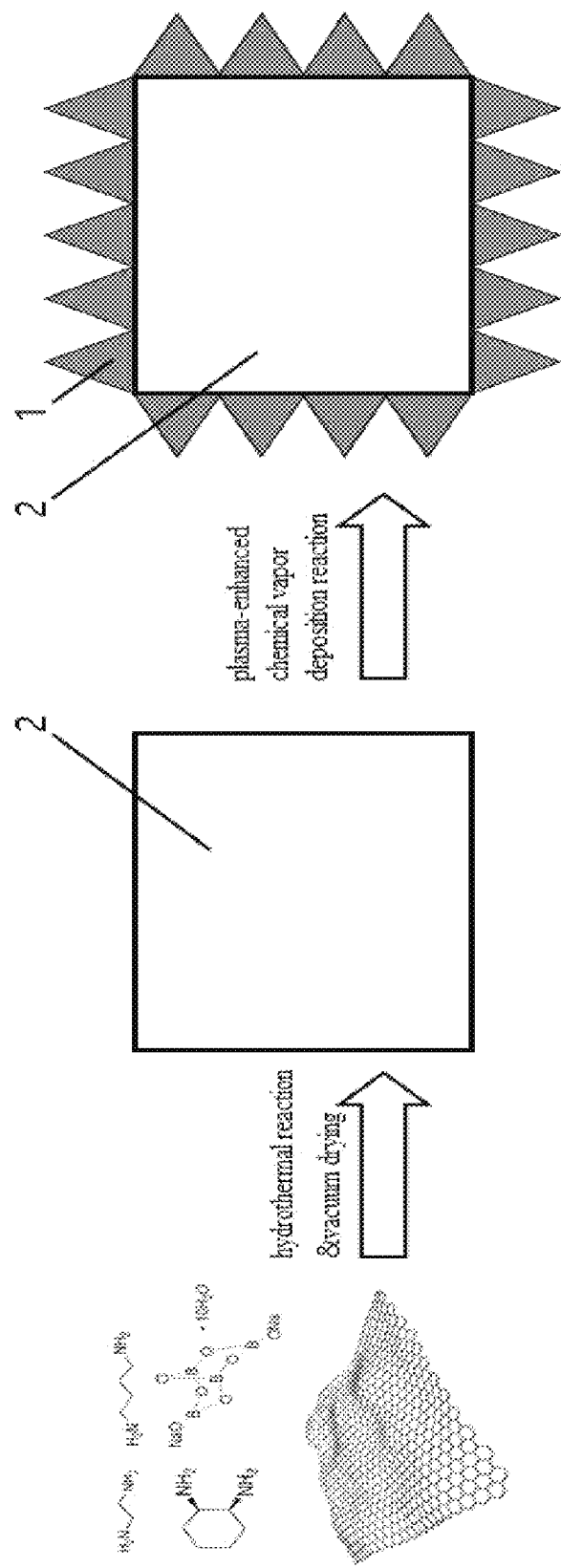
FIG. 2 is a preparation flow chart of the photothermal evaporation material integrating light absorption and thermal insulation provided by the present invention.

As shown in FIG. 2, the preparation process of the photothermal evaporation material integrating light absorption and thermal insulation provided by the present invention, that is, the vertically-oriented graphene/graphene foam comprises: the growth of the light absorber 1 and the synthesis of the heat insulator 2. First, the graphene foam with three-dimensional structure (i.e., heat insulator 2) was synthesized by hydrothermal method and freeze-drying method; then, by plasma-enhanced chemical vapor deposition technology, the external surface of the above graphene foam was covered with vertically-oriented graphite. During the preparation process, the vertically-oriented graphene was connected to the graphene foam by covalent bonds.

The photothermal evaporation material integrating light absorption and thermal insulation provided by the present invention is subjected to the following performance tests:

1. Water contact angle: a contact angle meter, whose model is DropMeter A-200, was used to measure the water contact angle of the photothermal evaporation material integrating light absorption and thermal insulation, to characterize the hydrophilicity of the material. Using an electric pump to drop 10 L of water on the surface of the material, a high-speed camera was used to record the changing process of water droplets, and the water contact angle was calculated by the Yang-Laplace equation.

2. Absorbance of light absorber: a UV-Visible spectrophotometer, whose model is UV-3150 UV-VIS, was used to measure the light transmittance and light reflectance of the photothermal evaporation material integrating light absorption and thermal insulation in the 200~2600 nm band. The Formula: light absorptance=1−light transmittance−light reflectance, was used to calculate the average light absorptance.

3. Thermal conductivity of the heat insulator: a laser thermal conductivity measuring instrument, whose model is LFA 467, was used to test the thermal conductivity of the photothermal evaporation material integrating light absorption and thermal insulation.

4. Types of surface functional groups: an X-ray photoelectron spectrometer, whose model is VG Escalab Mark II, was used to test the X-ray energy spectrum distribution and analyze the types of functional groups.

Example 1

1. An aqueous solution of graphene oxide was provided, wherein the concentration of graphene oxide was 4 g $L^{-1}$, the concentration of sodium tetraborate decahydrate was 1 mmol $L^{-1}$, and the concentration of ethylenediamine was 4 mmol $L^{-1}$.

2. The prepared aqueous solution of graphene oxide was transferred to a Teflon high temperature and high-pressure reactor, maintained at 90° C. for 6 hours, then maintained at 120° C. for 6 hours, and then cooled to room temperature to obtain a graphene hydrogel.

3. Soaking the obtained graphene hydrogel with ethanol aqueous solution for 6 hours, in which the volume fraction of ethanol was 10%, the purpose was to clean the additives remaining on the surface of the graphene hydrogel.

4. Transferring the washed graphene hydrogel to a freezing chamber with a temperature of −80° C., freezing for 6 hours, and then transferring to a drying chamber with a temperature of 0° C. and an air pressure of <650 Pa, and vacuum drying for 6 hours to obtain a graphene foam.

5. Placing the obtained graphene foam in the plasma-enhanced chemical vapor deposition reaction chamber, evacuating to <10 Pa, and then heating to 800° C.

6. Opening the $CH_4$ and $H_2$ gas valves to pass the mixture of $CH_4$ and $H_2$ flow, the flow ratio of $H_2$ was 5 ml $min^{-1}$, the flow ratio of $CH_4$ was 5 ml $min^{-1}$, and the air pressure was adjusted to 100 Pa.

7. Turning on the inductively coupled plasma source, adjusting the power to 250 W, and maintaining for 120 min.

8. Turning off the plasma source, closing the $CH_4$ and $H_2$ gas valves, opening the Ar gas valve to pass Ar as a cooling gas with a flow ratio of 10 ml $min^{-1}$. After cooling to room temperature, removing the vertically-oriented graphene/graphene foam.

9. The obtained vertically-oriented graphene/graphene foam composite was exposed to an environment with an ozone concentration of 200 ppm for 3 minutes, and the oxygen-containing functional groups were modified on the surface of the vertically-oriented graphene to construct a water flow channel. The oxygen-containing functional groups include —OH, —CHO, —COOH; specifically, ozone was generated by a dielectric barrier discharge device, and the air was used as the feeding gas; a photothermal evaporation material integrating light absorption and thermal insulation was obtained.

Figure 3:
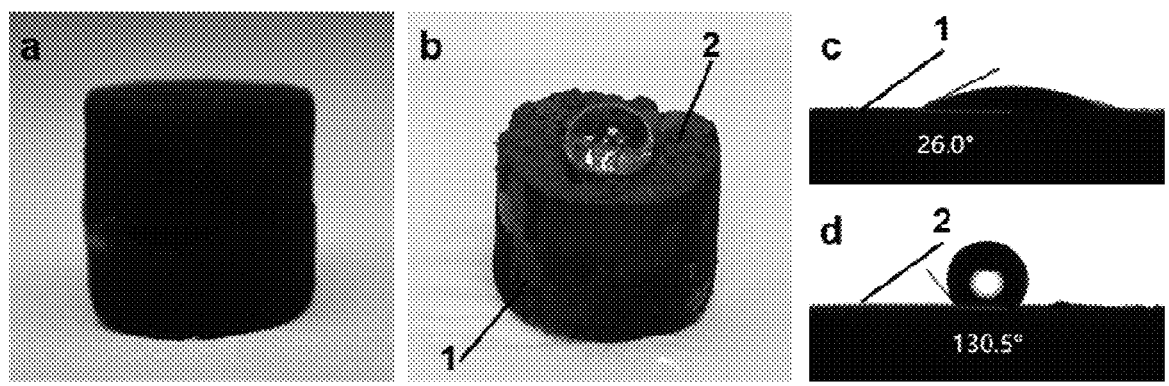
FIG. 3 is an optical diagram and wettability characterization results of the photothermal evaporation material integrating light absorption and thermal insulation provided in Example 1.

The optical diagram of the obtained photothermal evaporation material integrating light absorption and thermal insulation was shown as a in FIG. 3, and the external surface was black. The wettability of the vertically-oriented graphene/graphene foam modified with oxygen-containing functional groups on the surface was shown as b-d in FIG. 3, the outer vertically-oriented graphene 1 exhibited strong hydrophilicity, and the water contact angle was 26.0°, indicating the light absorber serves as a water flow channel, which can guide the transmission of water through capillary action; the internal of the graphene foam 2 exhibited strong hydrophobicity, and the water contact angle was 130.5°, indicating that the heat insulator repels the infiltration of water, and the surface water flow channel can protect the heat insulator from being wetted by water.

Figure 4:
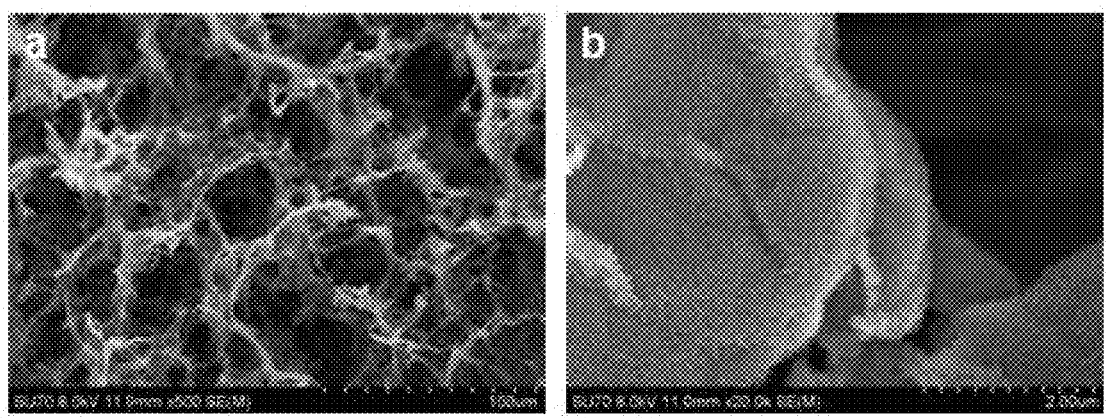
FIG. 4 is a scanning electron micrograph of the photothermal evaporation material integrating light absorption and thermal insulation provided in Example 1.

The microstructure of graphene foam was shown as a in FIG. 4, which showed a porous structure and low thermal conductivity, with thermal conductivity of 0.041 W $m^{-1}$ $K^{-1}$. The vertically-oriented graphene was composed of a carbon nanowall array, such as shown in b of FIG. 4, the vertically-oriented graphene was evenly distributed on the skeleton of the graphene foam; the vertically aligned carbon nanowall array can prevent the escape of incident light and has extremely strong light trapping ability.

Figure 5:
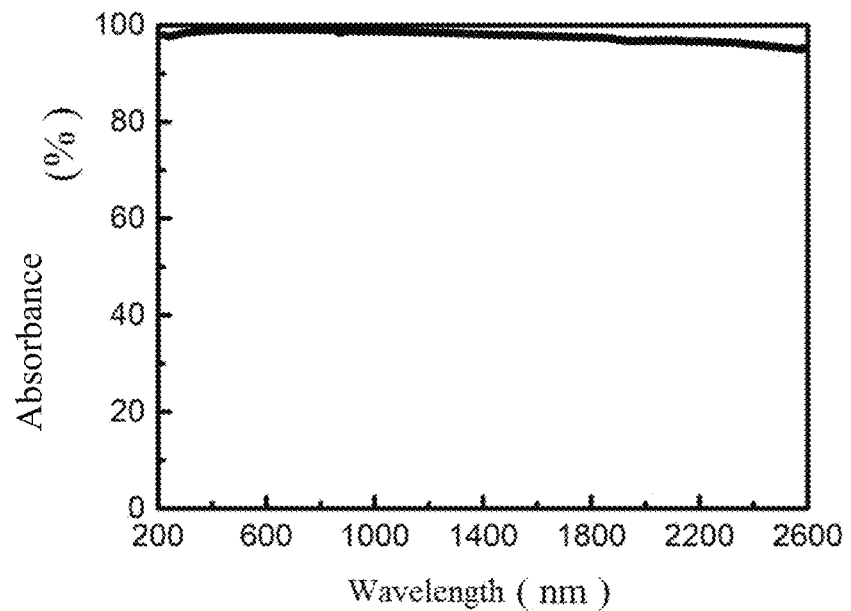
FIG. 5 is a light absorption curve of the photothermal evaporation material integrating light absorption and thermal insulation provided in Example 1.

As shown in FIG. 5, the average light absorptance of the obtained photothermal evaporation material integrating light absorption and thermal insulation in the wavelength band of 200-2600 nanometers was as high as 97.8%. In application, the photothermal evaporation material integrating light absorption and thermal insulation floated on the water surface, the light absorber captured solar energy, and converted the solar energy into thermal energy, generating local high temperature; the heat insulator blocked heat transfer and reduced heat dissipation; the heat insulator sucked the liquid through capillary action, so that the liquid reached the local high-temperature area, and realized rapid photothermal evaporation.

Figure 6:
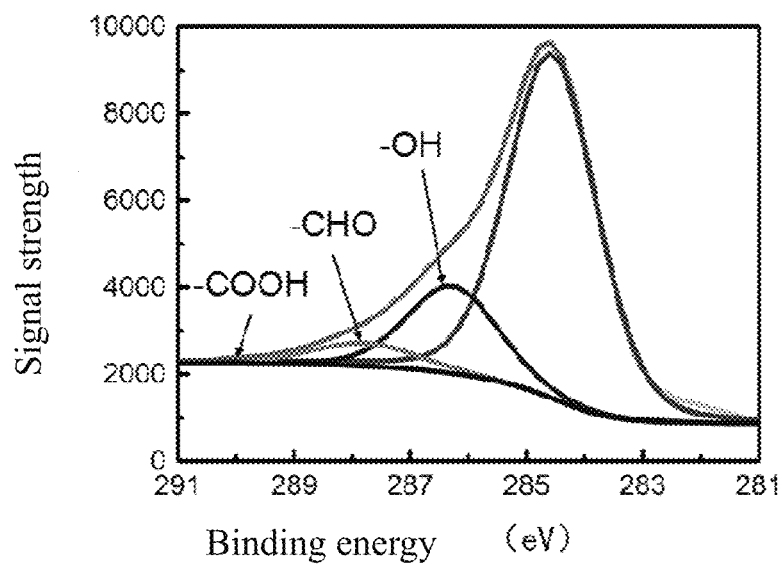
FIG. 6 is an X-ray photoelectron C1s energy spectrum of the photothermal evaporation material integrating light absorption and thermal insulation provided in Example 1.

As shown in FIG. 6, the surface-modified oxygen-containing functional groups of the obtained photothermal evaporation material integrating light absorption and thermal insulation included —OH, —CHO, and —COOH.

Figure 7:
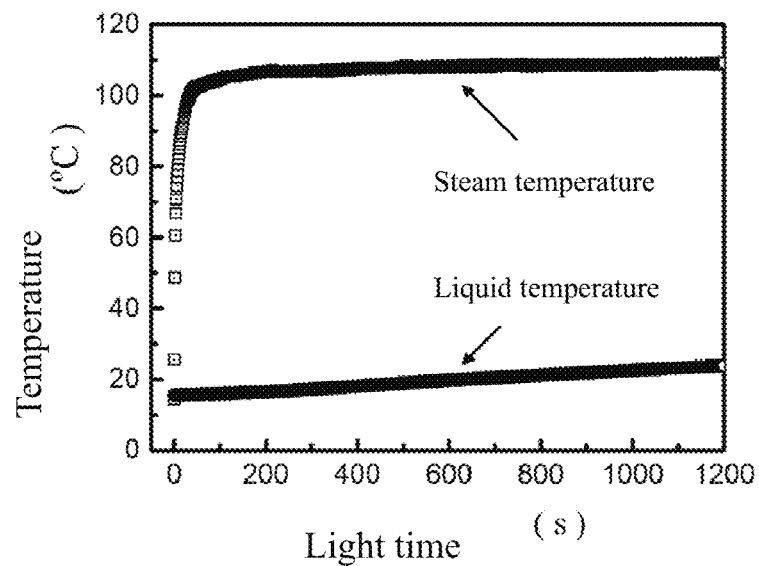
FIG. 7 is a photo-heat evaporation application effect diagram of the light-absorbing and heat-insulation integrated photo-heat evaporation material provided in Example 1.

As shown in FIG. 7, under the condition of light intensity of 10 kW $m^{-2}$, only 34 seconds, saturated water vapor>100° C. could be detected in the local high-temperature area of the material, while the water temperature was almost unchanged, And the steam generation rate of this material was as high as 12.3 kg $m^{-2}$ $h^{-1}$, and the corresponding photothermal conversion efficiency exceeded 90%.

Example 2

1. An aqueous solution of graphene oxide was provided, wherein the concentration of graphene oxide was 5 g $L^{-1}$, the concentration of sodium tetraborate decahydrate was 2 mmol $L^{-1}$, and the concentration of ethylenediamine was 8 mmol $L^{-1}$.

2. The prepared aqueous solution of graphene oxide was transferred to a Teflon high temperature and high-pressure reactor, maintained at 120° C. for 12 hours, and then cooled to room temperature to obtain a graphene hydrogel.

3. Soaking the obtained graphene hydrogel with an ethanol aqueous solution for 12 hours, in which the volume fraction of ethanol was 20%, the purpose was to clean the additives remaining on the surface of the graphene hydrogel.

4. Transferring the washed graphene hydrogel to a freezing chamber with a temperature of −60° C., freezing for 12 hours, and then transferring it to a drying chamber at a temperature of −10° C. and an air pressure of <650 Pa, and vacuum drying for 12 hours to obtain a graphene foam.

5. Placing the obtained graphene foam in the plasma-enhanced chemical vapor deposition reaction chamber, evacuating to <10 Pa, and then heating to 700° C.

6. Opening the $CH_4$ and $H_2$ gas valves to pass the mixture of $CH_4$ and $H_2$ flow, the flow ratio of $H_2$ was 5 ml min$^{-1}$, the flow ratio of $CH_4$ was 5 ml min$^{-1}$, and the air pressure was adjusted to 10 Pa.

7. Turning on the inductively coupled plasma source and the power to 250 W for 60 minutes.

8. Turning off the plasma source, closing the $CH_4$ and $H_2$ gas valves, opening the Ar gas valve to pass Ar as a cooling gas with a flow ratio of 10 ml min$^{-1}$. After cooling to room temperature, removing the vertically-oriented graphene/graphene foam.

9. The obtained vertically-oriented graphene/graphene foam was exposed to an environment with an ozone concentration of 200 ppm for 4 minutes, and the oxygen-containing functional groups were modified on the surface of the vertically-oriented graphene to construct a water flow channel. The oxygen-containing functional groups included —OH, —CHO, —COOH; where ozone was generated by a dielectric barrier discharge device, and the air was used as the feeding gas; a photothermal evaporation material integrating light absorption and thermal insulation was obtained.

The performance test results of the obtained photothermal evaporation material integrating light absorption and thermal insulation were shown in Table 1.

Example 3

1. An aqueous solution of graphene oxide was provided, wherein the concentration of graphene oxide was 5 g L$^{-1}$, the concentration of sodium tetraborate decahydrate was 3 mmol L$^{-1}$, and the concentration of ethylenediamine was 12 mmol L$^{-1}$.

2. The prepared aqueous solution of graphene oxide was transferred to a Teflon high temperature and high-pressure reactor, maintained at 90° C. for 6 hours, then maintained at 180° C. for 6 hours, and finally, cooled to room temperature to obtain a graphene hydrogel.

3. Soaking the obtained graphene hydrogel with an ethanol aqueous solution for 18 hours, wherein the volume fraction of ethanol was 20%, the purpose was to clean the additives remaining on the surface of the graphene hydrogel.

4. Transferring the washed graphene hydrogel to a freezing chamber with a temperature of −40° C., freezing for 18 hours, and then transferring it to a drying chamber at a temperature of −10° C. and an air pressure of <650 Pa, and vacuum drying for 24 hours to a obtain graphene foam.

5. Placing the obtained graphene foam in the plasma-enhanced chemical vapor deposition reaction chamber, evacuating to <10 Pa, and then heating to 650° C.

6. Opening the $CH_4$ and $H_2$ gas valves to pass the gas mixture of $CH_4$ and $H_2$, the flow ratio of $H_2$ was 40 ml min$^{-1}$, the flow ratio of $CH_4$ was 10 ml min$^{-1}$, and the air pressure was adjusted to 300 Pa.

7. Turning on the microwave plasma source and adjust the power to 500 W for 10 min.

8. Turn off the plasma source, close the $CH_4$ and $H_2$ gas valves, opening the $N_2$ gas valve to pass $N_2$ as a cooling gas with a flow ratio of 50 ml min$^{-1}$. After cooling to room temperature, removing the vertically-oriented graphene/graphene foam.

9. The obtained vertically-oriented graphene/graphene foam was exposed to an environment with an ozone concentration of 200 ppm for 2 minutes. and the oxygen-containing functional groups were modified on the surface of the vertically-oriented graphene to construct a water flow channel. The oxygen-containing functional groups included —OH, —CHO, —COOH; specifically, ozone was generated by a dielectric barrier discharge device and the air was used as the feeding gas; a photothermal evaporation material integrating light absorption and thermal insulation was obtained.

The performance test results of the obtained photothermal evaporation material integrating light absorption and thermal insulation were shown in Table 1.

Example 4

1. An aqueous solution of graphene oxide was provided, wherein the concentration of graphene oxide was 6 g L$^{-1}$, the concentration of sodium tetraborate decahydrate was 5 mmol L$^{-1}$, and the concentration of ethylenediamine was 20 mmol L$^{-1}$.

2. The prepared aqueous solution of graphene oxide was transferred to a Teflon high-temperature high-pressure reactor, maintained at 90° C. for 12 hours, then maintained at 180° C. for 6 hours, and then cooled to room temperature to obtain a graphene hydrogel.

3. Soaking the obtained graphene hydrogel with an ethanol aqueous solution for 24 hours, in which the volume fraction of ethanol was 30%, the purpose was to clean the remaining additives on the surface of the graphene hydrogel.

4. Transferring the washed graphene hydrogel to a freezing chamber with a temperature of −10° C., freezing for 24 hours, and then transfer it to a drying chamber at a temperature of −20° C. and an air pressure of <650 Pa, and vacuum drying for 48 hours to obtain a graphene foam.

5. Placing the obtained graphene foam in the plasma-enhanced chemical vapor deposition reaction chamber, evacuating to <10 Pa, and then heating to 600° C.

6. Opening the $CH_4$ and $H_2$ gas valves to pass the mixture of $CH_4$ and $H_2$ flow, the flow ratio of $H_2$ was 50 ml min$^{-1}$, the flow ratio of $CH_4$ was 10 ml min$^{-1}$, and the air pressure was adjusted to 500 Pa.

7. Turning on the microwave plasma source and adjusting the power to 500 W for 20 minutes.

8. Turning off the plasma source, closing the $CH_4$ and $H_2$ gas valves, opening the $N_2$ gas valve to pass $N_2$ as the cooling gas, the flow ratio was 100 ml min$^{-1}$. After cooling to room temperature, removing the vertically-oriented graphene/graphene foam.

9. The obtained vertically-oriented graphene/graphene foam was exposed to an environment with an ozone concentration of 200 ppm for 2 minutes, and the oxygen-containing functional groups were modified on the surface of the vertically-oriented graphene to construct a water flow channel. The oxygen-containing functional groups included —OH, —CHO, —COOH; specifically, ozone was generated by a dielectric barrier discharge device, and the air was used as the feeding gas. A photothermal evaporation material integrating light absorption and thermal insulation was obtained.

The performance test results of the obtained photothermal evaporation material integrating light absorption and thermal insulation were shown in Table 1.

Example 5

1. An aqueous solution of graphene oxide was provided, wherein the concentration of graphene oxide was 1 g $L^{-1}$.
2. The prepared aqueous solution of graphene oxide was transferred to a Teflon high temperature and high-pressure reactor, maintained at 120° C. for 6 hours, and then cooled to room temperature to obtain a graphene hydrogel.
3. Transferring the washed graphene hydrogel to a freezing chamber with a temperature of −10° C., freezing for 12 hours, and then transferring to a drying chamber at a temperature of −10° C. and an air pressure of <650 Pa, and vacuum drying for 12 hours to obtain a graphene foam.
4. Placing the obtained graphene foam in the plasma-enhanced chemical vapor deposition reaction chamber, evacuating to <10 Pa, and then heating to 500° C.
5. Opening the $CH_4$ and $H_2$ gas valves to pass the mixture of $CH_4$ and $H_2$ flow, the flow ratio of $H_2$ was 20 ml $min^{-1}$, the flow ratio of $CH_4$ was 1 ml $min^{-1}$, and the air pressure was adjusted to 10 Pa.
6. Turning on the inductively coupled plasma source and adjusting the power to 200 W for 180 min.
7. Turning off the plasma source, closing the $CH_4$ and $H_2$ gas valves, opening the Ar gas valve to pass Ar flow as a cooling gas with a flow ratio of 10 ml $min^{-1}$. After cooling to room temperature, removing the vertically-oriented graphene/graphene foam.
8. The obtained vertically-oriented graphene/graphene foam was exposed to an environment with an ozone concentration of 200 ppm for 10 minutes, and the oxygen-containing functional groups were modified on the surface of the vertically-oriented graphene to construct a water flow channel. The oxygen-containing functional groups included —OH, —CHO, —COOH; specifically, ozone was generated by a dielectric barrier discharge device, and the air was used as the feeding gas. A photothermal evaporation material integrating light absorption and thermal insulation was obtained.

The performance test results of the obtained photothermal evaporation material integrating light absorption and thermal insulation were shown in Table 1.

Example 6

1. An aqueous solution of graphene oxide was provided, wherein the concentration of graphene oxide was 10 g $L^{-1}$, the concentration of sodium tetraborate decahydrate was 10 mmol $L^{-1}$, and the concentration of ethylenediamine was 100 mmol $L^{-1}$.
2. The prepared aqueous solution of graphene oxide was transferred to a Teflon high temperature and high-pressure reactor, maintained at 120° C. for 12 hours, then maintained at 180° C. for 6 hours, and then cooled to room temperature to obtain a graphene hydrogel.
3. Soaking the obtained graphene hydrogel with an ethanol aqueous solution for 24 hours, in which the volume fraction of ethanol was 30%, the purpose was to clean the remaining additives on the surface of the graphene hydrogel.
4. Transferring the washed graphene hydrogel to a freezing chamber with a temperature of −80° C., freezing for 12 hours, and then transferring to a drying chamber at a temperature of −10° C. and an air pressure of <650 Pa, and vacuum drying for 12 hours to obtain a graphene foam.
5. Placing the obtained graphene foam in the plasma-enhanced chemical vapor deposition reaction chamber, evacuating to <10 Pa, and then heating to 1000° C.;
6. Opening the $CH_4$ gas valve to pass $CH_4$, the flow ratio of $CH_4$ was 1 ml $min^{-1}$ and the air pressure was adjusted to 1000 Pa.
7. Turning on the microwave plasma source and adjusting the power to 500 W for 1 min.
8. Turning off the plasma source, closing the $CH_4$ gas valve, opening the $N_2$ gas valve to pass $N_2$ as a cooling gas with a flow ratio of 50 ml $min^{-1}$. After cooling to room temperature, removing the vertically-oriented graphene/graphene foam.
9. The obtained vertically-oriented graphene/graphene foam was exposed to an environment with an ozone concentration of 200 ppm for 1 min, and the oxygen-containing functional groups were modified on the surface of the vertically-oriented graphene to construct a water flow channel. The oxygen-containing functional groups included —OH, —CHO, —COOH; specifically, ozone was generated by a dielectric barrier discharge device and the air was used as the feeding gas; a photothermal evaporation material integrating light absorption and thermal insulation was obtained.

The performance test results of the obtained photothermal evaporation material integrating light absorption and thermal insulation were shown in Table 1.

Example 7

1. An aqueous solution of graphene oxide was provided, wherein the concentration of graphene oxide was 6 g $L^{-1}$, the concentration of sodium tetraborate decahydrate was 1 mmol $L^{-1}$, and the concentration of butanediamine was 4 mmol $L^{-1}$;
2. The prepared aqueous solution of graphene oxide was transferred to a Teflon high temperature and high-pressure reactor, maintained at 90° C. for 6 hours, then maintained at 120° C. for 6 hours, and finally cooled to room temperature to obtain a graphene hydrogel;
3. Soaking the obtained graphene hydrogel with an ethanol aqueous solution for 12 hours, in which the volume fraction of ethanol was 20%, the purpose was to clean the additives remaining on the surface of the graphene hydrogel;
4. Transferring the cleaned graphene hydrogel to a freezing chamber with a temperature of −80° C., freezing for 12 hours, and then transfer to a drying chamber at a temperature of −10° C. and an air pressure of <650 Pa, and vacuum dry for 12 hours to obtain graphene foam;
5. Placing the obtained graphene foam in the plasma-enhanced chemical vapor deposition reaction chamber, evacuate to <10 Pa, and then heating to 800° C.;
6. Opening the $CH_4$ and $H_2$ gas valves, and letting the gas mixture of $CH_4$ and $H_2$ flow. The flow ratio of $H_2$ was 50 ml min−1, the flow ratio of $CH_4$ was 50 ml $min^{-1}$, and the air pressure was adjusted to 1000 Pa;
7. Turning on the DC glow discharge plasma source and adjusting the power to 500 W for 30 minutes;
8. Turning off the plasma source, closing the $CH_4$ and $H_2$ gas valves, opening the $N_2$ gas valve, pass $N_2$, as the cooling gas, the flow ratio was 50 ml $min^{-1}$, to be cooled to room temperature, taking out the vertically-oriented graphene/graphene foam;
9. The obtained vertically-oriented graphene/graphene foam was exposed to an environment with an ozone concentration of 200 ppm for 5 minutes, and the oxygen-containing functional groups were modified on the surface of the vertically-oriented graphene to construct a water flow channel. The oxygen-containing functional groups included —OH, —CHO, —COOH; where ozone was generated by a dielectric barrier discharge device, and the air was used as the feeding gas; a photothermal evaporation material integrating light absorption and thermal insulation was obtained.

The performance test results of the obtained photothermal evaporation material integrating light absorption and thermal insulation were shown in Table 1.

Example 8

1. An aqueous solution of graphene oxide was provided, wherein the concentration of graphene oxide was 6 g $L^{-1}$, the concentration of sodium tetraborate decahydrate was 2 mmol $L^{-1}$, and the concentration of butanediamine was 4 mmol $L^{-1}$.

2. The prepared aqueous solution of graphene oxide was transferred to a Teflon high temperature and high-pressure reactor, maintained at 120° C. for 12 hours, and then cooled to room temperature to obtain a graphene hydrogel.

3. Soaking the obtained graphene hydrogel with an ethanol aqueous solution for 12 hours, in which the volume fraction of ethanol was 20%, the purpose was to clean the additives remaining on the surface of the graphene hydrogel.

4. Transferring the washed graphene hydrogel to a freezing chamber with a temperature of –80° C., freezing for 12 hours, and then transferring to a drying chamber at a temperature of –10° C. and an air pressure of <650 Pa, and vacuum drying for 12 hours to obtain a graphene foam.

5. Placing the obtained graphene foam in the plasma-enhanced chemical vapor deposition reaction chamber, evacuating to <10 Pa, and then heating to 700° C.

6. Opening the $CH_4$ and $H_2$ gas valves to pass the mixture of $CH_4$ and $H_2$ flow, the flow ratio of $H_2$ was 5 ml $min^{-1}$, the flow ratio of $CH_4$ was 5 ml $min^{-1}$, and the air pressure was adjusted to 100 Pa.

7. Turning on the microwave plasma source, adjusting the power to 250 W, and maintaining for 1 min.

8. Turning off the microwave plasma source, closing the $CH_4$ and $H_2$ gas valves, opening the Ar gas valve to pass Ar as a cooling gas with a flow ratio of 20 ml $min^{-1}$. After cooling to room temperature, removing the vertically-oriented graphene/graphene foam.

9. The obtained vertically-oriented graphene/graphene foam was exposed to an environment with an ozone concentration of 200 ppm for 3 minutes, and the oxygen-containing functional groups were modified on the surface of the vertically-oriented graphene to construct a water flow channel. The oxygen-containing functional groups include —OH, —CHO, —COOH; specifically, ozone was generated by a dielectric barrier discharge device, and the air was used as the feeding gas; a photothermal evaporation material integrating light absorption and thermal insulation was obtained.

The performance test results of the obtained photothermal evaporation material integrating light absorption and thermal insulation were shown in Table 1.

Example 9

1. An aqueous solution of graphene oxide was provided, wherein the concentration of graphene oxide was 6 g $L^{-1}$, the concentration of sodium tetraborate decahydrate was 3 mmol $L^{-1}$; the concentration of hexamethylenediamine was 4 mmol $L^{-1}$.

2. The prepared aqueous solution of graphene oxide was transferred to a Teflon high temperature and high-pressure reactor, maintained at 90° C. for 6 hours, then maintained at 180° C. for 6 hours, and then cooled to room temperature to obtain a graphene hydrogel;

3. Soaking the obtained graphene hydrogel with an ethanol aqueous solution for 12 hours, in which the volume fraction of ethanol was 20%, the purpose was to clean the additives remaining on the surface of the graphene hydrogel;

4. Transferring the washed graphene hydrogel to a freezing chamber with a temperature of –80° C., freezing for 12 hours, and then transferring to a drying chamber at a temperature of –10° C. and an air pressure of <650 Pa, and vacuum drying for 12 hours to obtain a graphene foam;

5. Placing the obtained graphene foam in the plasma-enhanced chemical vapor deposition reaction chamber, evacuating to <10 Pa, and then heating to 700° C.;

6. Opening the $CH_4$ and $H_2$ gas valves to pass the mixture of $CH_4$ and $H_2$ flow, the flow ratio of $H_2$ was 5 ml $min^{-1}$, the flow ratio of $CH_4$ was 5 ml $min^{-1}$, and the air pressure was adjusted to 100 Pa;

7. Turning on the inductively coupled plasma source, adjusting the power to 250 W, and maintaining for 60 minutes;

8. Turning off the microwave plasma source, closing the $CH_4$ and $H_2$ gas valves, opening the Ar gas valve to pass Ar flow as a cooling gas with a flow ratio of 20 ml $min^{-1}$. After cooling to room temperature, removing the vertically-oriented graphene/graphene foam;

9. The obtained vertically-oriented graphene/graphene foam was exposed to an environment with an ozone concentration of 200 ppm for 3 minutes, and the oxygen-containing functional groups were modified on the surface of the vertically-oriented graphene to construct a water flow channel. The oxygen-containing functional groups include —OH, —CHO, —COOH; specifically, ozone was generated by a dielectric barrier discharge device, and the air was used as the feeding gas; a photothermal evaporation material integrating light absorption and thermal insulation was obtained.

The performance test results of the obtained photothermal evaporation material integrating light absorption and thermal insulation were shown in Table 1.

Example 10

1. An aqueous solution of graphene oxide was provided, wherein the concentration of graphene oxide was 6 g $L^{-1}$, the concentration of sodium tetraborate decahydrate was 4 mmol $L^{-1}$, and the concentration of cyclohexanediamine was 4 mmol $L^{-1}$.

2. The prepared aqueous solution of graphene oxide was transferred to a Teflon high temperature and high-pressure reactor, maintained at 120° C. for 6 hours, then maintained at 180° C. for 6 hours, and then cooled to room temperature to obtain a graphene hydrogel.

3. Soaking the obtained graphene hydrogel with an ethanol aqueous solution for 12 hours, in which the volume fraction of ethanol was 20%, the purpose was to clean the additives remaining on the surface of the graphene hydrogel.

4. Transferring the washed graphene hydrogel to a freezing chamber with a temperature of –80° C., freezing for 12 hours, and then transferring to a drying chamber at a temperature of –10° C. and an air pressure of <650 Pa, and vacuum drying for 12 hours to obtain a graphene foam.

5. Placing the obtained graphene foam in the plasma-enhanced chemical vapor deposition reaction chamber, evacuating to <10 Pa, and then heating to 700° C.

6. Opening the $CH_4$ and $H_2$ gas valves to pass the mixture of $CH_4$ and $H_2$ flow, the flow ratio of $H_2$ was 5 ml min$^{-1}$, the flow ratio of $CH_4$ was 5 ml min$^{-1}$, and the air pressure was adjusted to 100 Pa.

7. Turning on the inductively coupled plasma source, adjusting the power to 250 W, and maintaining for 30 minutes.

8. Turning off the microwave plasma source, closing the $CH_4$ and $H_2$ gas valves, open the Ar gas valve to pass Ar flow as a cooling gas with a flow ratio of 20 ml min$^{-1}$. After cooling to room temperature, removing the vertically-oriented graphene/graphene foam;

9. The obtained vertically-oriented graphene/graphene foam was exposed to an environment with an ozone concentration of 200 ppm for 3 minutes, and the oxygen-containing functional groups were modified on the surface of the vertically-oriented graphene to construct a water flow channel. The oxygen-containing functional groups include —OH, —CHO, —COOH; specifically, ozone was generated by a dielectric barrier discharge device, and the air was used as the feeding gas; a photothermal evaporation material integrating light absorption and thermal insulation was obtained.

The performance test results of the photothermal evaporation material integrating light absorption and thermal insulation prepared in Examples 1-10 were shown in Table 1.

to form an integrated structure. Seawater was injected into the evaporation chamber 3 through the water inlet 5 of the evaporation chamber. The photothermal evaporation material 2 was put into the evaporation chamber 3 from above and floated on the seawater. The upper surface height of the photothermal evaporation material 2 was always lower than the minimum height of the inlet of the extraction channel 11 to prevent seawater from flowing to the collection chamber 4 through the extraction channel 11 and the steam guiding conduit 9. The light-transmissive condensation plate 1 covers the evaporation chamber 3 at an inclination angle of 30°, which not only serves to close the evaporation chamber 3 but also condense the water vapor and guide the condensate water to the collection chamber 4. The photothermal evaporation material 2 absorbed solar energy and converts the solar energy into thermal energy to evaporate seawater. The extraction fan 10 drew the steam in the evaporation chamber 3 into the extraction channel 11, and guided the steam to the collection chamber 4 through the steam guiding conduit 9. During the operation of the device, the water inlet 5 and water outlet 7 of the evaporation chamber and the water inlet 6 and water outlet 8 of the collection chamber remained closed. After the device stopped working, the fresh water obtained can be transferred and used through the water outlet 8 of the collection chamber.

Figure 11:
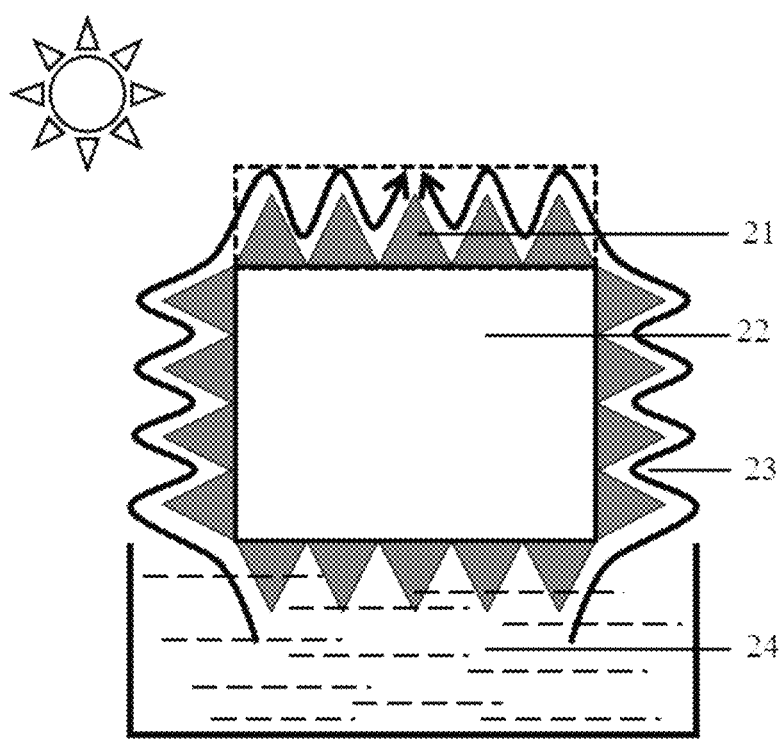
FIG. 11 is a schematic diagram of the principle of photothermal evaporation of the solar photothermal seawater desalination device provided in Example 11-20 and the high-temperature steam sterilization device provided in Example 21-30.

As shown in FIG. 11, the photothermal evaporation material 2 comprises a heat insulator 22 and a light absorber 21 covering the external surface of the heat insulator 22. The light absorber 21 was vertically-oriented graphene whose surface was modified with hydrophilic functional groups.

TABLE 1

Performance test results of the photothermal evaporation material integrating light absorption and thermal insulation prepared in Examples 1-10

| Examples | Water contact angle of the light absorber ° | Water contact angle of the heat insulator ° | Absorbance of light absorber % | Thermal conductivity of the heat insulator W m$^{-1}$ K$^{-1}$ | photothermal conversion efficiency |
|---|---|---|---|---|---|
| Example 1 | 26.0 | 130.5 | 97.8% | 0.041 | 91.6% |
| Example 2 | 18.2 | 120.7 | 97.0% | 0.038 | 91.1% |
| Example 3 | 20.5 | 129.0 | 98.2% | 0.033 | 92.0% |
| Example 4 | 22.4 | 133.4 | 97.0% | 0.031 | 91.0% |
| Example 5 | 0 | 101.2 | 94.9% | 0.180 | 86.6% |
| Example 6 | 33.2 | 134.5 | 90.0% | 0.051 | 85.0% |
| Example 7 | 10.1 | 114.5 | 94.6% | 0.060 | 86.1% |
| Example 8 | 25.2 | 131.4 | 97.4% | 0.041 | 89.0% |
| Example 9 | 24.5 | 129.7 | 94.4% | 0.037 | 87.1% |
| Example 10 | 22.5 | 127.8 | 93.0% | 0.029 | 85.3% |

Examples 11-20

Figure 8:
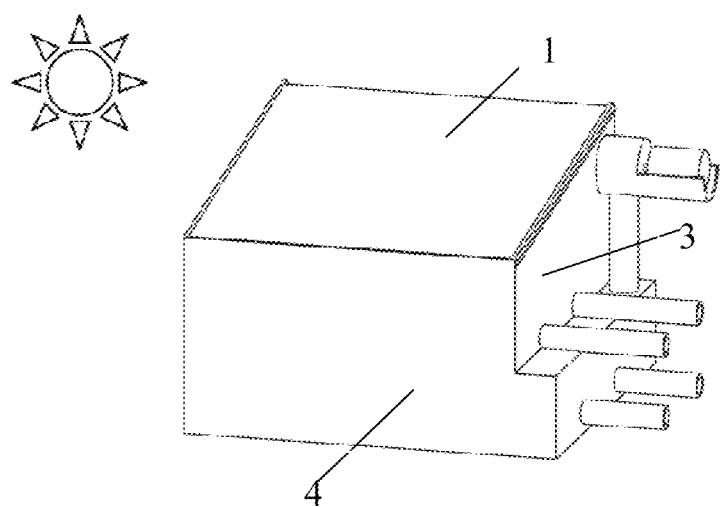
FIG. 8 is a schematic structural view of a solar photothermal seawater desalination device provided in Examples 11-20.
Figure 9:
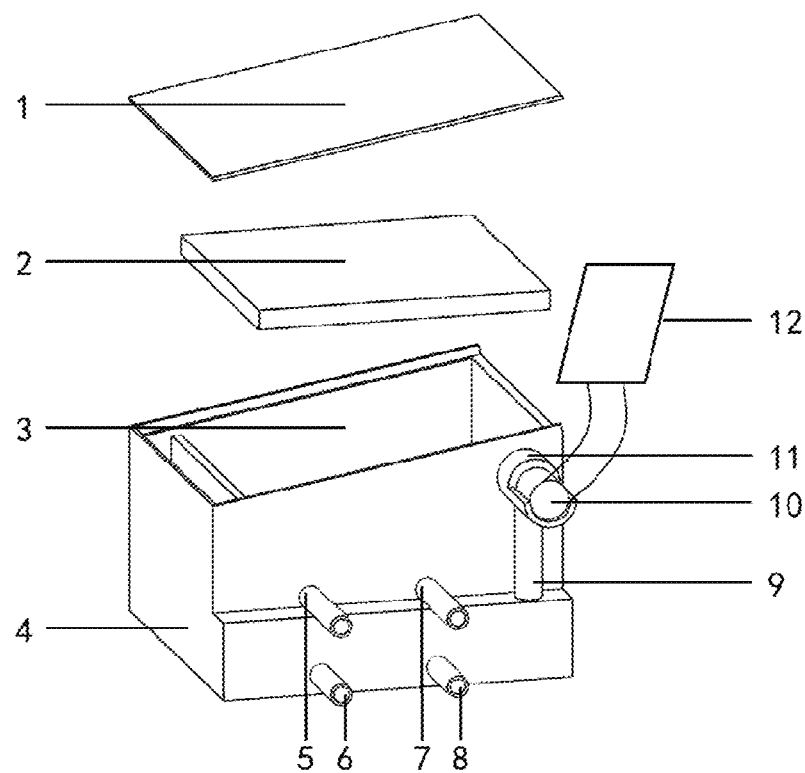
FIG. 9 is a schematic diagram of an exploded structure of a solar photothermal seawater desalination device provided in Examples 11-20.
Figure 10:
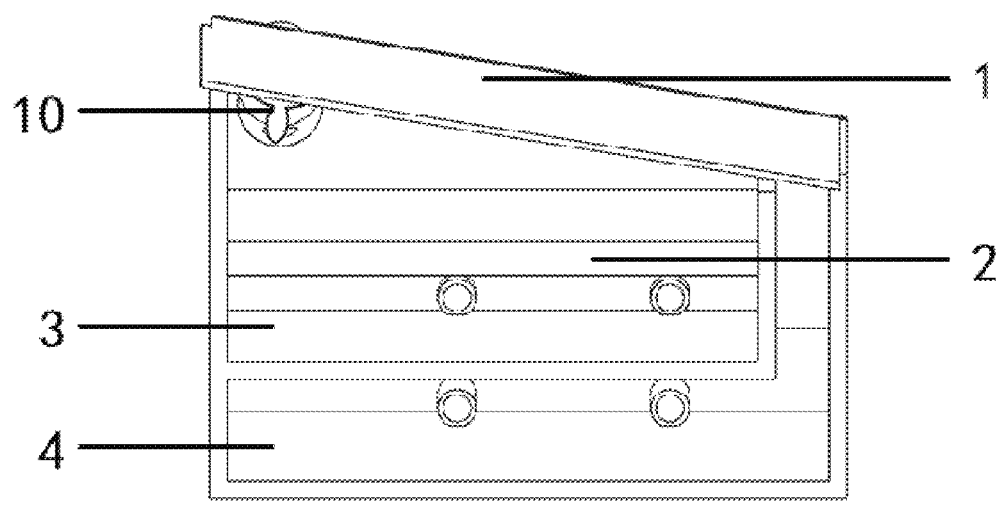
FIG. 10 is a schematic cross-sectional structural diagram of a solar photothermal seawater desalination device provided in Examples 11-20.

As shown in FIG. 8, FIG. 9 and FIG. 10, the solar photothermal seawater desalination device provided in Examples 11-20 comprises: a light-transmissive condensation plate 1, a photothermal evaporation material 2, an evaporation chamber 3, a collection chamber 4, and a water inlet 5 of the collection chamber 4, a water inlet 6 of the collection chamber 4, a water outlet 7 of the evaporation chamber, a water outlet 8 of the collection chamber, a steam guiding conduit 9, an extraction fan 10, an extraction channel 11, and a solar panel 12.

The extraction fan 10 was installed in the extraction channel 11 on the side wall of the evaporation chamber 3, and was driven by the electric energy provided by the solar panel 12 for continuous operation. The evaporation chamber 3 and the collection chamber 4 were distributed up and down The heat insulator 22 was a graphene foam, and the vertically-oriented graphene and graphene foam were connected in the form of covalent bonds; the light absorber 21 was vertically-oriented graphene whose surface was modified with hydrophilic functional groups.

The light absorber 21 captured solar energy and converted solar energy into thermal energy to generate a local high temperature; the heat insulator 22 blocked heat transport and reduced heat dissipation. At the same time, the light absorber 21 also served as a liquid flow channel 23 to transport liquid 24 to a local high-temperature area through capillary action, so as to achieve rapid photothermal evaporation. At the same time, the liquid flow channel 23 can protect the heat insulator 22 from being wetted by the liquid 24 and prevent the heat flow loss caused by the infiltrated liquid 24.

The photothermal evaporation materials 2 in Examples 11-20 were the photothermal evaporation material integrating light absorption and thermal insulation prepared in Examples 1-10, respectively.

Using the solar photothermal seawater desalination device provided in Example 11-20, the natural seawater with a salinity of 3.25% was subjected to evaporative condensation treatment, and the salinity of the obtained condensate water was 0.01%, which met the drinking water requirements; the natural seawater with a salinity of 9.85% was subjected to evaporative condensation treatment, and the salinity of the obtained condensate water was 0.01%, which meets the drinking water requirements; the natural seawater with a salinity of 16.7% was subjected to evaporative condensation treatment, and the salinity of the obtained condensate water was 0.02%, which meets drinking water requirements.

The performance test results of the solar photothermal seawater desalination device provided in Examples 11-20 were shown in Table 2.

capillary action, so as to achieve rapid photothermal evaporation. At the same time, the liquid flow channel 23 can protect the heat insulator 22 from being wetted by the liquid 24 and prevent the heat flow loss caused by the infiltrated liquid 24.

Figure 12:
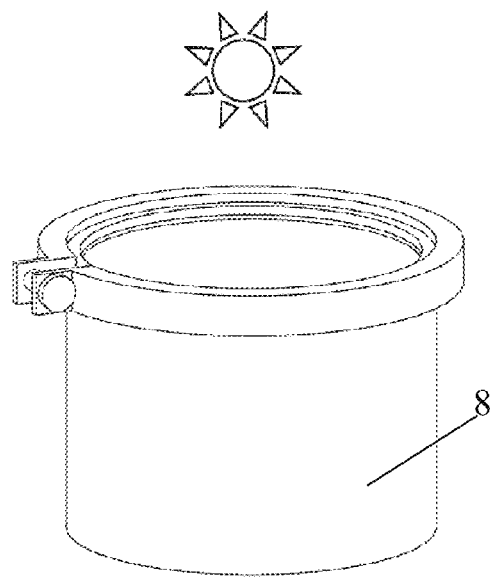
FIG. 12 is a schematic structural diagram of a high-temperature steam sterilization device provided in Examples 21-30.
Figure 13:
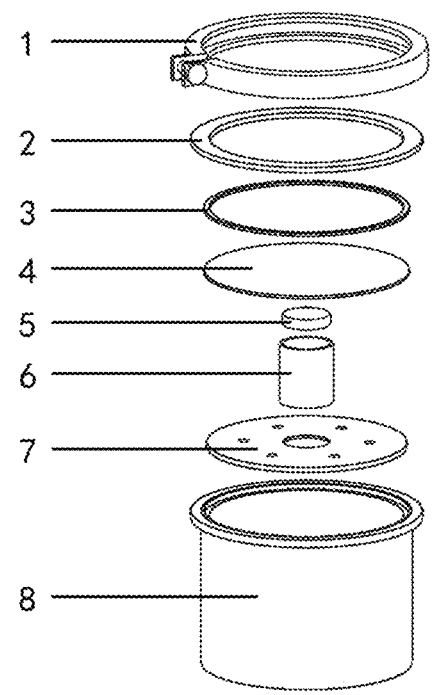
FIG. 13 is a schematic diagram of the decomposition structure of the high-temperature steam sterilization device provided in Examples 21-30.
Figure 14:
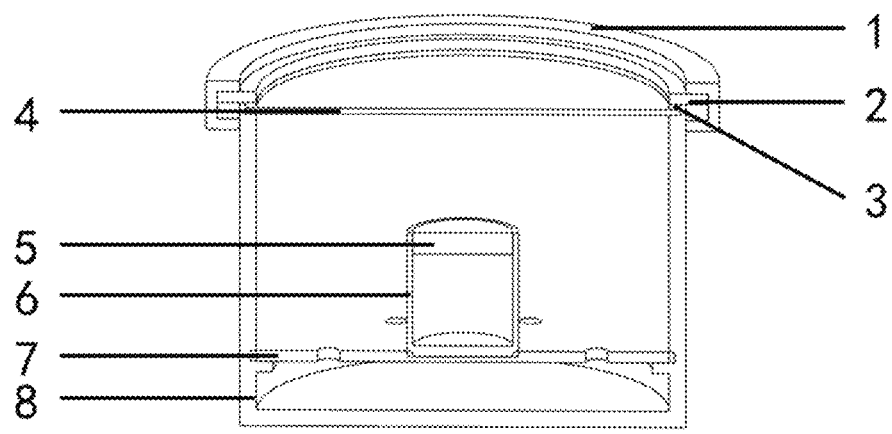
FIG. 14 is a schematic cross-sectional structural diagram of a high-temperature steam sterilization device provided in Examples 21-30.

As shown in FIG. 12, FIG. 13 and FIG. 14, the loading tray 7 was placed on the pallet of the evaporation chamber 8; the water storage cup 6 was placed in the groove in the center of the loading tray 7; a certain amount of water was added to the water storage cup 6, and the photothermal evaporation material 2 was put into the water storage cup 6 from above, the photothermal evaporation material 2 floated on the surface of the water; the items to be sterilized was placed on the loading tray 7 in the evaporation chamber 8; then the optical concentrator 4 was covered on the evaporation chamber 8, and the evaporation chamber 8 was closed with a sealing ring 3, a fixing ring 2 and a clamp 1.

The photothermal evaporation materials 2 in Examples 21-30 were the photothermal evaporation material integrating light absorption and thermal insulation prepared in Examples 1-10, respectively.

TABLE 2

Performance test results of the solar photothermal seawater desalination device provided in Examples 11-20

| Examples | Water contact angle of the light absorber ° | Water contact angle of the heat insulator ° | Absorbance of light absorber % | Thermal conductivity of the heat insulator $Wm^{-1}K^{-1}$ | Photothermal conversion efficiency | Salinity after desalination | | |
|---|---|---|---|---|---|---|---|---|
| | | | | | | Salinity before desalination 3.25% | Salinity before desalination 9.85% | Salinity before desalination 16.7% |
| Example11 | 26.0 | 130.5 | 97.8% | 0.041 | 91% | 0.01% | 0.01% | 0.02% |
| Example12 | 18.2 | 120.7 | 97.0% | 0.038 | 90.1% | 0.01% | 0.02% | 0.02% |
| Example13 | 20.5 | 129.0 | 98.2% | 0.033 | 91.4% | 0.01% | 0.01% | 0.02% |
| Example14 | 22.4 | 133.4 | 97.0% | 0.031 | 90.5% | 0.01% | 0.01% | 0.02% |
| Example15 | 0 | 101.2 | 94.9% | 0.180 | 83.7% | 0.02% | 0.02% | 0.02% |
| Example16 | 33.2 | 134.5 | 90.0% | 0.051 | 84.4% | 0.01% | 0.01% | 0.01% |
| Example17 | 10.1 | 114.5 | 94.6% | 0.060 | 85.3% | 0.01% | 0.02% | 0.02% |
| Example18 | 25.2 | 131.4 | 97.4% | 0.041 | 88.4% | 0.01% | 0.02% | 0.02% |
| Example19 | 24.5 | 129.7 | 94.4% | 0.037 | 86.4% | 0.01% | 0.02% | 0.02% |
| Example20 | 22.5 | 127.8 | 93.0% | 0.029 | 85.0% | 0.01% | 0.02% | 0.02% |

Examples 21-30

As shown in FIG. 12, FIG. 13 and FIG. 14, the high-temperature steam sterilization device provided in Examples 21-30 comprises: a clamp 1, a fixing ring 2, a sealing ring 3, an optical concentrator 4, a photothermal evaporation material 5, a storage water cup 6, a loading tray 7, a steam chamber 8.

As shown in FIG. 11, the photothermal evaporation material 2 comprises a heat insulator 22 and a light absorber 21 covering the external surface of the heat insulator 22. The light absorber 21 was vertically-oriented graphene whose surface was modified with hydrophilic functional groups. The heat insulator 22 was graphene foam, and the vertically-oriented graphene and graphene foam were connected in the form of covalent bonds; the light absorber 21 was vertically-oriented graphene whose surface was modified with hydrophilic functional groups.

Figure 15:
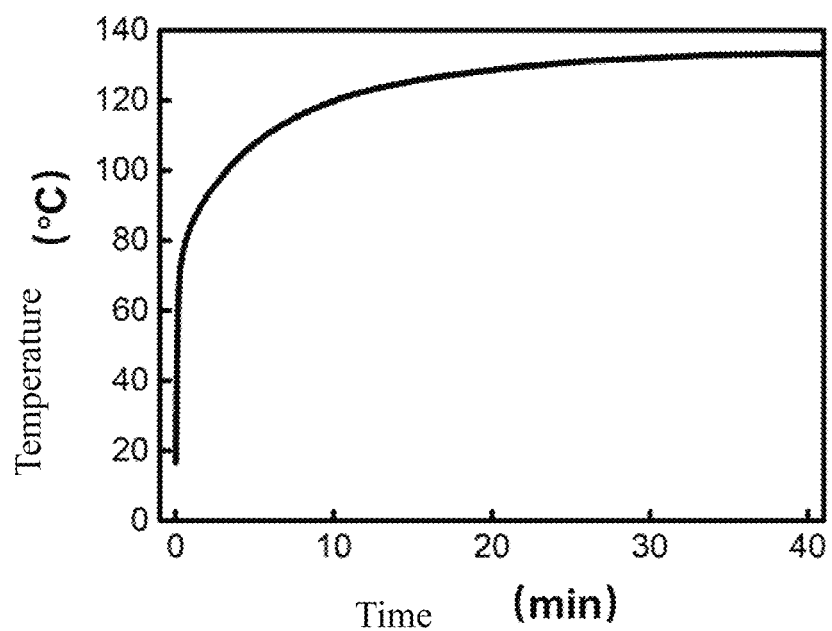
FIG. 15 is the steam temperature during the sterilization process of the high-temperature steam sterilization device provided in Example 21.

The light absorber 21 captured solar energy and converted solar energy into thermal energy to generate a local high temperature. The heat insulator 22 blocked heat transport and reduced heat dissipation. At the same time, the light absorber 21 also served as a liquid flow channel 23 to transport liquid 24 to a local high-temperature area through Using the high-temperature steam sterilization device provided in Example 21, operating under natural light, the light intensity was 1.0-1.2 kW m−2, using a standard biological indicator as a test of sterilization effect, when the indicator color changes from purple to yellow, it indicated that the sterilization has failed. When the color of the indicator remains purple, it indicated that the sterilization has succeeded. As shown in FIG. 15, after 11 minutes of operation, the temperature in the evaporation chamber reaches 121° C., which was the expected sterilization temperature. According to the WHO standard, maintaining a high-temperature steam environment of 121° C. for 30 minutes can achieve sufficient disinfection and destruction. Therefore, after 41 minutes of operation, the work was stopped. The biological indicator after sterilization was transferred to 56° C. environment and incubated for 48 h. After observation, the indicator without sterilization was yellow, and the indicator after sterilization was purple, indicating successful sterilization.

The performance test results of the high-temperature steam sterilization device provided in Examples 21-30 were shown in Table 3.

TABLE 3

Performance test results of the high-temperature steam sterilization device provided in Examples 21-30

| Examples | Water contact angle of the light absorber ° | Water contact angle of the heat insulator ° | Absorbance of light absorber % | Thermal conductivity of the heat insulator W Wm$^{-1}$ K$^{-1}$ | Sterilization time min | Sterilization effect |
|---|---|---|---|---|---|---|
| Example21 | 26.0 | 130.5 | 97.8% | 0.041 | 41 | Success |
| Example22 | 18.2 | 120.7 | 97.0% | 0.038 | 48 | Success |
| Example23 | 20.5 | 129.0 | 98.2% | 0.033 | 43 | Success |
| Example24 | 22.4 | 133.4 | 97.0% | 0.031 | 50 | Success |
| Example25 | 0 | 101.2 | 94.9% | 0.180 | 70 | Success |
| Example26 | 33.2 | 134.5 | 90.0% | 0.051 | 74 | Success |
| Example27 | 10.1 | 114.5 | 94.6% | 0.060 | 60 | Success |
| Example28 | 25.2 | 131.4 | 97.4% | 0.041 | 57 | Success |
| Example29 | 24.5 | 129.7 | 94.4% | 0.037 | 62 | Success |
| Example30 | 22.5 | 127.8 | 93.0% | 0.029 | 65 | Success |

The above is a detailed description of the present invention in combination with examples, but the implementation of the present invention is not limited by the above examples. Any other changes, replacements, and combination simplifications made under the core guiding idea of the patent of the present invention are included in this Within the scope of protection of invention patents.

The invention claimed is:

1. A photothermal evaporation material integrating light absorption and thermal insulation comprises a heat insulator and a light absorber that covers the external surface of the heat insulator, wherein the light absorber is vertically-oriented graphene, the heat insulator is a graphene foam, and the vertically-oriented graphene and graphene foam are connected by covalent bonds; the light absorber is vertically-oriented graphene whose surface is modified with hydrophilic functional groups; wherein the hydrophilic functional groups are oxygen-containing functional groups; and wherein the oxygen-containing functional groups are hydroxyl (—OH), aldehyde group (—CHO), and carboxyl (—COOH); and wherein absorbance of the light absorber is 90-99%, and thermal conductivity of the heat insulator is 0.02-0.2 W m$^{-1}$ K$^{-1}$.

2. A solar photothermal seawater desalination device, wherein the solar photothermal seawater desalination device comprises a light-transmissive condensation plate, an evaporation chamber, and a collection chamber in order from top to bottom; the evaporation chamber being arranged on top of the collection chamber to form an integrated structure; the light-transmissive condensation plate covers the evaporation chamber and guides condensed water to the collection chamber; the photothermal evaporation material according to claim 1 is placed in the evaporation chamber;

wherein the solar photothermal seawater desalination device further comprises an extraction channel and a steam guiding conduit, one end of the extraction channel is connected to the evaporation chamber, the other end is connected to the collection chamber through the steam guiding conduit; a suction channel and the steam guiding conduit are provided on the side wall of the evaporation chamber; and wherein the inclination angle of the light-transmissive condensation plate is 10°-60°.

3. A high-temperature steam sterilization device maintaining a high-temperature steam environment of 121° C., wherein the high-temperature steam sterilization device comprises a steam chamber, an optical concentrator covering the steam chamber, a loading tray and a water storage cup installed inside the steam chamber, and a photothermal evaporation material in the water storage cup; the photothermal evaporation material is the photothermal evaporation material integrating light absorption and thermal insulation according to claim 1;

wherein the loading tray has a plurality of through holes in the vertical direction; the optical concentrator focuses the light beam into the water storage cup; the cross-sectional shape of the optical concentrator and the water storage cup are the same, and the cross-sectional area ratio is 10-100:1, and the optical concentrator and the water storage cup are assembled concentrically; and wherein the steam chamber is provided with a pallet for mounting the loading tray.

4. A method for fabricating the photothermal evaporation material integrating light absorption and thermal insulation according to claim 1, comprises the following steps:

(1) preparing an aqueous solution of graphene oxide;

(2) transferring the aqueous solution of graphene oxide obtained in step (1) to a high temperature and high-pressure reactor for hydrothermal reaction, and cooling to obtain a graphene hydrogel;

(3) soaking the graphene hydrogel obtained in step (2) with an ethanol aqueous solution;

(4) transferring the graphene hydrogel to a freezing chamber for freezing, and then transferring to a drying chamber for vacuum drying to obtain a graphene foam;

(5) placing the obtained graphene foam in a plasma-enhanced chemical vapor deposition reaction chamber, and introducing methane or a mixture of hydrogen and methane; after the chemical vapor deposition reaction, the inert gas is introduced for cooling to obtain the vertically-oriented graphite/graphene foam;

(6) exposing the vertically-oriented graphene/graphene foam obtained in step (5) to an ozone environment, and the hydrophilic functional groups are modified on the surface of the vertically-oriented graphene to obtain a photothermal evaporation material integrating light absorption and thermal insulation.

5. The method for fabricating a photothermal evaporation material integrating light absorption and thermal insulation according to claim 4, wherein the aqueous solution of graphene oxide in step (1) further comprises an additive, and the additive comprises sodium tetraborate decahydrate, amine compound or mixtures thereof; the concentration of the graphene oxide is 1-10 g $L^{-1}$, the concentration of the sodium tetraborate decahydrate is 0-10 mmol $L^{-1}$, the concentration of the amine compound is 0-100 mmol $L^{-1}$; and the concentration of the sodium tetraborate decahydrate and the concentration of the amine compound are not 0 at the same time.

6. The method for fabricating a photothermal evaporation material integrating light absorption and thermal insulation according to claim 5, wherein the conditions of hydrothermal reaction in step (2) are: the reaction temperature is 90-180° C.; the reaction time is 6-18 hours.

7. The method for fabricating a photothermal evaporation material integrating light absorption and thermal insulation according to claim 4, wherein in step (5), the flow ratio of the gas mixture of hydrogen and methane is 0-20:1.

8. The method for fabricating a photothermal evaporation material integrating light absorption and thermal insulation according to claim 4, wherein in step (5), the reaction conditions of the chemical vapor deposition reaction are: the synthesis temperature is 500-1000° C., the synthetic gas pressure is 10-1000 Pa.

9. A method for seawater desalination, sewage purification, and high-temperature steam sterilize comprising the step of utilizing the photothermal evaporation material integrating light absorption and thermal insulation according claim 1.

* * * * *